United States Patent [19]
Breitbach et al.

[11] Patent Number: 6,087,450
[45] Date of Patent: Jul. 11, 2000

[54] WATER-SWELLING POLYMERS CROSS-LINKED WITH UNSATURATED AMINO ALCOHOLS, THE PRODUCTION AND USE OF SAME

[75] Inventors: Ludger Breitbach, Duisburg; Kurt Dahmen, Mönchengladbach; Jochen Houben, Kempen; Erich Küster, Krefeld, all of Germany

[73] Assignee: Stockhausen GmbH & Co., KG, Krefeld, Germany

[21] Appl. No.: 09/068,562

[22] PCT Filed: Nov. 18, 1996

[86] PCT No.: PCT/EP96/05073

§ 371 Date: May 20, 1998

§ 102(e) Date: May 20, 1998

[87] PCT Pub. No.: WO97/18889

PCT Pub. Date: May 29, 1997

[30] Foreign Application Priority Data

Nov. 21, 1995 [DE] Germany ............................ 195 43 366

[51] Int. Cl.[7] .............................. C08F 16/08; C08F 16/28
[52] U.S. Cl. ...................... 525/242; 525/259; 525/328.8; 525/63; 525/64; 525/69
[58] Field of Search .................................. 525/242, 259, 525/328.8, 63, 64, 69

[56] References Cited

U.S. PATENT DOCUMENTS 5,314,420  5/1994  Smith et al. .

FOREIGN PATENT DOCUMENTS 0 668 080    8/1995   European Pat. Off. .
63-199205    8/1988   Japan .
WO 94/25519  11/1994  WIPO .

*Primary Examiner*—Duc Truong
*Attorney, Agent, or Firm*—Oblon, Spivak, McClelland, Maier & Neustadt, P.C.

[57] ABSTRACT

The present invention relates to cross-linked polymers absorbing aqueous liquids, which are built up of partially neutralized, mono-ethylenically unsaturated, acid groups-containing monomers, optionally further monomers copolymerizable with these, as well as optional polymers suitable as a graft basis, and that can be produced by using cross-linking agents of polyunsaturated amino alcohols. The used cross-linking agents are reaction products of (meth) allylamines with monoglycidyl compounds, di-, tri- or tetraglycidyl compounds, and optional alkylene oxide; reaction products of (meth)allylamines or saturated primary amines with (meth)acrylglycide esters and/or (meth)allyl glycidyl ethers and optional alkylene oxide; as well as reaction products of di- and polyamides with (meth)allyl glycide esters and/or (meth)acrylglycide esters and optional alkylene oxide. The polymers according to the present invention provide superabsorbers whose property level meets the practice-oriented requirements with respect to retention, absorption under pressure, swelling pressure, and permeability for aqueous liquids. Such polymers are used as absorbents for water and aqueous liquids in constructions for the absorption or body fluids, in current-conducting and light-transmitting cables, and in the cultivation of plants.

46 Claims, No Drawings

WATER-SWELLING POLYMERS CROSS-LINKED WITH UNSATURATED AMINO ALCOHOLS, THE PRODUCTION AND USE OF SAME

The present invention relates to superabsorbent polymers for aqueous liquids, to a process for their production and to their use. The polymers based on carboxylate groups-containing monomers are obtained by using cross-linking agents based on unsaturated amino alcohols which, because of their structure, are active in both radical preliminary cross-linkage and thermal secondary cross-linkage. The cross-linked superabsorbent polymers have excellent properties.

Superabsorbent polymers are water-insoluble, cross-linked polymers which, under swelling and formation of hydrogels, are capable of absorbing large amounts of aqueous liquids and body fluids, such as urine or blood, and of retaining the absorbed liquid amount under a certain pressure. Owing to these characteristic absorption properties, the polymers are mainly used to incorporate them into sanitary articles, such as diapers and sanitary napkins, and in the cultivation of plants.

Commercially available superabsorbent polymers are mainly cross-linked polyacrylic acids or cross-linked starch/acrylic acid-graft co-polymers wherein the carboxyl groups are partially neutralized with sodium or potassium ions.

Superabsorbent polymers are mainly produced by polymerizing aqueous solutions of mixtures made of partially neutralized acrylic acid and cross-linker into a polymer gel which—after mechanical comminution—is dried and ground to a particular particle size. Alternatively, polymer powders may also be obtained by inverse suspension polymerization wherein the aqueous monomer phase is suspended with auxiliary agents in an oil phase, for example consisting of cyclohexane, and is subsequently polymerized.

The characteristic features of superabsorbers can be improved by secondary surface cross-linkage, in particular with respect to their liquid absorption under pressure; the known phenomenon of "gel blocking" where swollen polymer particles agglutinate and thus impair further liquid absorption and liquid distribution within the diaper is suppressed. During secondary cross-linkage the carboxyl groups of the polymer molecules are cross-linked at the surface of the superabsorber particles with cross-linking agents at elevated temperatures. Among others, multivalent metallic salts, glycidyl compounds, polyols, polyepoxides, polyamines, alkylene carbonates, and polyethylene glycols are used as cross-linking agents. The secondary cross-linking step may also be carried out repeatedly.

In the course of advancing superabsorbent polymers, the requirements made on these products have substantially changed in the last years. Initially, only the very high swelling capacity on contact with liquids had been the main factor in the development of superabsorbers; however, it was found later that, in addition to the liquid amount to be absorbed, the stability of the swollen gel is also of importance. The aim must be a balanced relation between retention and gel strength so that in practice liquid absorption may also take place against a pressure. This specific absorption property is referred to as absorption under pressure/load in EP 339 461. The method of determining the liquid absorption under load (AUL) is carried out with differing loads. With increasing requirements made on superabsorbers, it was found that the initial test load of 21 $g/cm^2$ (0.3 psi) no longer measures the desired property standard necessary for incontinence products or diaper constructions with a low fluff content and large amounts of superabsorber. For this reason, application-proven pressure loads of 42 $g/cm^2$ (0.6 psi) and 49 $g/cm^2$ (0.7 psi) are also measured today.

In addition to a high level of retention and liquid absorption under load, superabsorbers must comprise small amounts of soluble constituents; these arise as a result of incomplete cross-linkage during polymerization reactions, and in use they are not completely retained in the polymer body. This finally reduces the superabsorber's capability of absorbing and distributing liquids in the diaper. For example, U.S. Re. 32,649 mentions as limit values for low soluble contents 7.5% after 1 hour and 17% after 16 hours.

The permeability of the swollen superabsorber for aqueous liquids represents another important property parameter. The higher the swollen superabsorber's permeability for aqueous liquids is, the less can it form so-called barrier layers blocking further transport of liquids in diapers. The method of determining the permeability is described in EP 640 330 A1 (pages 19–21) as "Gel Layer Permeability Test" (GLP).

In the past, the functional properties of superabsorbent polymers were optimized primarily by varying the kind and amount of cross-linking agents, by the pH-value during polymerization, and by aftertreating the polymer particles in terms of coating and/or secondary surface cross-linking.

Improved gel stability with low soluble contents is achieved in U.S. Re 32,649 by means of acid polymerization. The production method according to Re 32,649 has substantial deficiencies. On the one hand, there is an inefficiently low time/space-yield owing to low starting concentrations and several hours of afterheating the polymer gel; on the other hand, subsequent neutralization of the rigid polymer gel is very time consuming, and the quality obtained by neutralizing the preceding solution cannot be achieved. In general, subsequently neutralized polymer gels are not neutralized uniformly, and because of nonuniform alkali distribution they are frequently discolored. Severe variations in product quality may also occur as a result of nonuniform neutralization. Among a variety of possible cross-linkers, di- and polyesters of unsaturated mono- and polycarboxylic acids with polyols, bisacrylamides, di- or triallylamines are preferred, N,N-methylenebisacrylamide, trimethylolpropane triacrylate, and triallyvamine being mentioned as particularly preferred ones.

The object of WO 94/09043 is to provide new superabsorbent polymers having an increased absorption capacity for aqueous liquids, even under pressure load. To achieve this object, it describes double-cross-linked superabsorbers which are produced in a first step by cross-linking during polymerization with methylenebisacrylamide, bis(acrylamido) acetic acid, allyl acrylate, allyl methacrylate, esters or amides with terminal vinyl and allyl functions, or with highly ethoxylated trimethylolpropane triacrylate; in a second step the surface of the resultant polymer particles is coated with a cross-linker, followed by cross-linking.

WO 93/21237 describes superabsorbent polymers which are cross-linked with unsaturated esters of polyalkyl glycols; their properties are improved in a subsequent heating step with respect to retention and liquid absorption under a low pressure of 21 g/cm² (0.3 psi) to 25 g/g. Ethoxylated trimethylolpropane triacrylate is the preferred cross-linker, and the number of EO-units per polyglycol chain may be in the range of 2 and 8. According to the statements in this publication, the properties of superabsorbers cross-linked with non-ethoxylated trimethylolpropane triacrylate are very poor.

WO 95/02002 describes powdery, water-swellable, cross-linked polymers having a high absorption capacity for aqueous liquids, in particular body fluids, under load, which are formed of at least 50 mol-% of neutralized acid-groups-containing monomers, optionally copolymerizable monomers, a cross-linking agent, and optionally water-soluble polymers. The polymers are produced by adding to the monomers carbon dioxide as blowing agent and subsequent polymerization, drying and re-cross-linking with a secondary cross-linker. A particular improvement of the absorption rate is achieved by adding carbon dioxide.

It is the object of the present invention to provide new cross-linking agents and polymers cross-linked with them, as well as a process for their production; these are suitable as superabsorbers in diaper constructions or other technical applications. Moreover, it is the object to provide with these new cross-linked structures superabsorbers whose properties meet the practice-oriented requirements made on retention, absorption under pressure/load [49 g/cm² (0.7 psi)], swelling pressure, and permeability GLP of the swollen absorber gel for aqueous liquids.

This object is achieved by using cross-linking agents which are characterized by the fact that by means of reacting a glycide compound with unsaturated amines, for example, allylamines, they open the epoxide ring, thereby forming a hydroxyl group which is optionally available for a subsequent ethoxylation. There are also other reaction paths to produce the cross-linking agents according to the present invention; for example, reacting amines with unsaturated glycide compounds, such as (meth)allyl glycidyl ethers or glycidyl (meth)acrylates. In accordance with the different reaction possibilities of producing these cross-linker structures, the following general formulae I to IV may be used to describe the cross-linking agents:

General Formula I for reaction products of (meth)allylamines, monoglycidyl compounds and optional alkylene oxides:

| $H_oR_3(NR_1R_2)_p$ | | |
|---|---|---|
| $R_1, R_2$: | $CHR=CH-CH_2$, H | for o = 0 is p = 2 |
| R: | H, $CH_3$ | for o = 1 is p = 1 |
| $R_3$: | $R_a-C(H)_c(R_6)-CH_2$ | |
| $R_a$: | monovalent for c = 0: | H |
| | divalent for c = 1: | $CH_2$, |
| | | $OCH_2$, |
| | | $C_{1-6}-O-(CHR-CHR-O)_d$, |
| | | d = 1–45 | with the proviso that at least 2 residues $R_1, R_2$ mean $CHR=CH-CH_2$

| $C_{1-6}-CO-O-(CHR-CHR-O)_d$ | | |
|---|---|---|
| $R_6$: | $R_7H$ | |
| $R_7$: | O, $O(CHR-CHR-O)_n$ | n: 1 to 45 |

General Formula II for reaction products of (meth)allylamines, di-, tri-, or tetraglycidyl compounds, and optional alkylene oxides:

| $R_8(NR_1R_2)_2$ | | |
|---|---|---|
| $R_1, R_2$: | $CHR=CH-CH_2$, H | |
| R: | H, $CH_3$ | |
| $R_8$: | $CH_2-CH(R_6)-CH_2-O-R_4-CH_2-CH(R_6)-CH_2$ | |
| $R_4$: | $(CHR-CHR-O)_m$, | m = 1 to 45 |
| | $C_1-C_6-O$, | |
| | $R_5(O-R_3-NR_1R_2)_r-O$ | |
| | | r = 0: if diglycide compounds are used |
| | | r = 1: if triglycide compounds are used |
| | | r = 2: if tetraglycide compounds are used |
| $R_5$: | alkylene residue of a polyol, optionally with one or two OH-functions which may optionally be reacted with up to 45 moles of alkylene oxide. | |
| $R_3$: | $CH_2-CH(R_6)-CH_2$ | |
| $R_6$: | $R_7H$ | |
| $R_7$: | O, $O(CHR-CHR-O)_n$ | n: 1 to 45 | with the proviso that at least 2 residues $R_1, R_2$ mean $CHR=CH-CH_2$.

General Formula III for reaction products of (meth)allylamines or saturated primary amines with (meth)acrylglycide esters and/or (meth)allyl glycidyl ethers and optional alkylene oxides:

| $(R_9-R_3)_aN(B)_c(R_1)_j(R_2)_k$ | | |
|---|---|---|
| B: | $C_1-C_6$-alkyl | for c = 0 the following is valid: |
| $R_9$: | $CHR=CH-CH_2-O$, | for a = 1 is j = 1 and k = 1 |
| | $CH_2=CR-CO-O$ | for a = 2 is j = 1 and k = 0 |
| $R_1, R_2$: | $CHR=CH-CH_2$, H | for a = 3 is j and k = 0 |
| R: | H, $CH_3$ | |

-continued $$(R_9\text{—}R_3)_a N(B)_c (R_1)_j (R_2)_k$$

| | | |
|---|---|---|
| $R_3$: | $CH_2$—$CH(R_6)$—$CH_2$ | forc=1thefollowingisvalid: |
| $R_6$: | $R_7H$ | for a = 1 is j = 1 and k = 0 |
| | $R_7$: O, O(CHR—CHR—O)$_n$ | a = 2 is j and k = 0 |
| | n: 1 to 45 | |

General formula IV for reaction products of di- and polyamines with (meth)allyl glycidyl ethers and/or (meth)acrylglycide esters and optional alkylene oxides:

$$R_{11}[N(A)_b\text{—}(R_3\text{—}R_9)_p]_z$$

| | |
|---|---|
| | for b = 1 is p = 1 |
| | for b = 0 is p = 2 |
| | z = 2, 3, 4 |
| A: | H, $C_1$–$C_6$-alkyl |
| $R_3$: | $CH_2$—$CH(R_6)$—$CH_2$ |
| $R_6$: | $R_7H$ |
| | $R_7$: O, O(CHR—CHR—O)$_n$   n: 1 to 45 |
| | R: H, $CH_3$ |
| $R_9$: | CHR=CH—$CH_2$—O, |
| | $CH_2$=CR—CO—O |
| $R_{11}$: | di-, tri- or tetravalent alkylene residue of the amine component (mixed or individually aliphatic, cycloaliphatic, aromatic, heterocyclic). |

Suitable reaction components to produce the unsaturated amino alcohol-cross-linking agents according to the present invention, for example, include the following ones:

Amino components:

Aliphatic as well as aromatic, heterocyclic and cyclic compounds are used as suitable amino components for the reaction with the glycide compounds according to formulae I to IV, for example, methallylamine, allylamine, alkyl (meth)allylamines, e.g., methyl allylamine, methyl methallylamine, ethyl methallylamine, and ethyl allylamine; methyl-, ethyl-, propyl- and butylamine, diallylamine, dimethallylamine, aniline, ethylenediamine, diethylenetriamine, hexamethylenediamine, trimethylhexamethylenediamine, neopentane diamine, 1,2-propylenediamine, 4,7-dioxadecane-1,10-diamine, 4,9-dioxadodecane-1,12-diamine, polyether diamines, polyalkylene glycol diamines, 3-amino-1-methylaminopropane, bis (3-aminopropyl)methylamine, isophorone diamine, 4,4'-diaminodicyclohexylmethane, 1-(2-aminoethyl)piperazine, o-, m-, or p-phenylenediamine, 4,4'-diaminodiphenyimethane, 1,4-diaminoanthraquinone, 2,4,6-triamino-1,3,5-triazine, and their mixtures.

Glycide compounds: The glycide compounds to be used according to the present invention may be mono-, di- or polyfunctional. Examples of monofunctional compounds used alone or in admixture include: ethylene glycol monoglycide ether and the related $C_1$–$C_6$-alkyl ethers or esters; glycidol, ethylene oxide, propylene oxide, (meth) allyl glycidyl ethers, polyethylene glycol monoglycide ethers and the related $C_1$–$C_6$-alkyl ethers or esters; vinyl glycide ethers, glycidyl(meth)acrylates, glycidyl(meth)allyl ethers, or 1-halogen-2,3-epoxypropane. Ethylene glycol or polyglycol diglycide ethers; glycerol, trimethylolpropane, or pentaerythritol triglycide ethers; polyglycerol polyglycide ethers, sorbitol polyglycide ethers, or their mixtures are used as multifunctional glycide ethers. The above-mentioned polyethylene glycol chains of the glycide compounds may comprise up to 45, preferably up to 20, and most preferably up to 12 ethylene glycol units.

According to a preferred embodiment the cross-linking agents according to the present invention are alkoxylated at the free hydroxyl group. To this end, the alcohols according to the present invention are reacted, for example, with ethylene or propylene oxide or their mixtures. The alcohols are preferably reacted with ethylene oxide. This can also achieve an improved water solubility of the cross-linker. Up to 45 moles EO, preferably up to 20 moles EO, and most preferably up to 12 moles EO are added per hydroxyl group.

Some examples of cross-linking agents according to the present invention include diallylaminoethanol, diallylaminopolyglycol ether, 1,3-bis(diallylamino)-2-propanol, N,N-diallylamino-1-amino-3-allyloxy-2-propanol, polyethylene glycol di(N,N-diallyl-3-amino-2-hydroxy-prop-1-yl)ether, ethylene glycol di(N,N-diallyl-3-amino-2-hydroxy-prop-1-yl)ether, alkoxylated 1,3-bis(diallylamino)-2-propanol, alkoxylated 1-allyloxy-3-(diallylamino)-2-propanol, alkoxylated polyethylene glycol di(N,N-diallyl-3-amino-2-hydroxy-prop-1-yl) ether, alkoxylated ethylene glycol di(N, N-diallyl-3-amino-2-hydroxy-prop-1-yl)ether, N,N-di (allyloxy-2-hydroxy-prop-3-yl)aniline, alkoxylated N,N-di (allyloxy-2-hydroxy-prop-3-yl)aniline. The above-mentioned polyethylene glycol ether units preferably comprise a maximum of 45 moles of ethylene oxide, preferably a maximum of 20, and most preferably a maximum of 15 moles of ethylene oxide. According to another preferred embodiment the N-atoms of the cross-linkers are partially or completely quaternized. The cross-linkers or their mixtures to be used according to the present invention are used in amounts of 0.01 to 3.0%-wt., preferably 0.05 to 1.5%-wt., and most preferably 0.1 to 1.0%-wt., relative to the monomers.

According to another preferred embodiment, using mixtures of highly and low-alkoxylated cross-linking agents to be used according to the present invention has proved successful in cross-linking the superabsorbers according to the present invention.

Owing to the thermal treatments effected during the further absorber production process, for example, gel drying, the cross-linking agents according to the present invention surprisingly result in secondary cross-linking reactions improving the property profile of superabsorbers. This opens up the possibility of omitting the usual secondary surface cross-linkage or at least of reducing the amount of secondary cross-linker. The efficiency of this secondary cross-linkage, wherein the carboxylate groups of the polymer particle are cross-linked, can be increased by the ethoxylation of free OH-groups according to the present invention.

To modify the superabsorbers' properties further, other cocross-linkers may optionally be used in amounts of up to 1.0%-wt., preferably 0.01–0.8%-wt., and most preferably up to 0.05–0.4%-wt., relative to the monomers. Preferred cocross-linkers are those comprising at least two ethylenically unsaturated double-bonds, for example, methylenebisacrylamide or -methacrylamide or ethylenebisacrylamide; additionally, esters of unsaturated mono- or polycarboxylic acids of polyols, such as, diacrylates or triacrylates, e.g., butanediol- or ethylene glycol diacrylate or -methacrylate; trimethylolpropane triacrylate, as well as their alkoxylates; additionally, allyl compounds, such as allyl (meth)acrylate, triallyl cyanurate, maleic acid diallyl ester, polyallyl ester, tetraallyloxyethane, di- and triallylamine, tetrallylethylenediamine, allyl esters of phosphoric acid or phosphorous acid. Moreover, compounds having at least one functional group reactive towards acid groups may also be used. Examples thereof include N-methylol compounds of amides, such as methacrylamide or acrylamide, and the ethers derived therefrom, as well as di- and polyglycidyl compounds.

The aqueous liquids-absorbing polymer to be used according to the present invention is obtained by polymerizing ethylenically unsaturated, acid groups-containing monomers, for example, of acrylic acid, methacrylic acid, vinyl acetic acid, maleic acid, 2-acrylamido-2-methylpropane sulfonic acid, vinyl sulfonic acid, (meth)allyl sulfonic acid, or their mixtures, in the presence of the cross-linking agents according to the present invention. The proportion of these acid monomers amounts to 55–99%-wt. in the monomer mixture.

The acid monomers are neutralized to the extent of at least 25 mol-%, preferably at least 50 mol-%, and most preferably 50 to 80 mol-%, and they are then present, for example, as sodium, potassium, or ammonium salt or their mixtures. Neutralization is effected either by adding the corresponding alkali or ammonium hydroxides, or with the corresponding carbonates or hydrogen carbonates.

For property modification, the polymers according to the present invention may optionally comprise further comonomers which are substantially soluble in the aqueous monomer solution. Examples thereof include (meth)acrylamide, (meth)acrylonitrile, vinyl pyrrolidone, vinyl acetamide, hydroxyethyl acrylate, alkyl polyethylene glycol (meth) acrylates, alkylaminoalkyl (meth)acrylates, alkylaminopropyl acrylamides, acrylamidopropyl trimethylammonium chloride, or their mixtures. Such comonomers should not exceed a proportion of 40%-wt., relative to the acid monomers, because they could impair swellability of the superabsorber.

The polymers according to the present invention may comprise water-soluble polymers as graft basis in amounts of up to 30%-wt., relative to the amount of present monomers. Among others, these include partially or completely saponified polyvinyl alcohols, starch or starch derivatives, cellulose or cellulose derivatives, polyacrylic acids, polyglycols, or their mixtures. The molecular weights of the polymers added as graft basis must be adapted to the circumstances of the polymerization conditions. In the case of an aqueous solution polymerization, it may, for example, be necessary to use only low or medium-molecular polymers due to the viscosity of the polymer solution, while in suspension polymerization this factor is of minor importance.

The addition of natural and/or synthetic fibers results in a faster liquid absorption and an increased retention of the superabsorber according to the present invention.

In principle, the superabsorbers according to the present invention are manufactured according to two methods:

According to the first method, the partially neutralized acrylic acid is converted in aqueous solution in the presence of the cross-linking agents according to the present invention and optional further cross-linking agents and polymer additives, into a gel by radical polymerization; this is then comminuted, dried, ground, re-cross-linked, and screened out to the desired particle size. Solution polymerization may be carried out continuously or discontinuously. Patent literature discloses a wide spectrum of variations with respect to concentration ratios, temperatures, kind and amount of initiators, as well as a great variety of secondary cross-linking possibilities. Typical methods are described in the following patent documents which are incorporated in the production method according to the present invention by reference: U.S. Pat. No. 4,076,663, U.S. Pat. No. 4,286,082, DE 27 06 135, DE 35 03 458, DE 40 20 780, DE 42 44 548, DE 43 23 001, DE 43 33 056, DE 44 18 818.

The second method is the inverse suspension and emulsion polymerization. In these processes, an aqueous, partially neutralized acrylic acid solution is dispersed in a hydrophobic organic solvent by means of protective colloids and/or emulsifiers, and the polymerization is started by radical initiators. The cross-linking agents are either dissolved in the monomer solution and fed together with it, or they are added separately and optionally afterwards. The optionally present polymeric graft bases are added via the monomer solution or by direct addition to the oil phase. After termination of the polymerization, the water is azeotropically removed from the reaction mixture, and the polymeric product is filtered off.

A surface cross-linkage of the polymer particles can be effected either in the suspension or subsequently with the isolated polymer powder. The process principle is described, for example, in U.S. Pat. No. 4,340,706, DE 37 13 601, DE 28 40 010 and is incorporated in the production method according to the present invention by reference.

Polyols, polyepoxides, polyamines, or alkylene carbonates are particularly suitable as secondary cross-linkers.

It is often advantageous to add the secondary cross-linkers in the form of a solution in water, organic solvents or their mixtures, in particular when small amounts of a secondary cross-linking agent are used. Suitable mixers to apply the secondary cross-linking agent include, for example, Patterson-Kelley-mixers, DRAIS-turbulent mixers, Lödige-mixers, Ruberg-mixers, screw mixers, pan mixers, and fluidized-bed mixers, as well as continuous vertical mixers wherein the powder is mixed at high speed by means of rotary knives (Schugi-mixers). After mixing the secondary cross-linker with the preliminarily cross-linked polymer, heating to temperatures of 120 to 250° C., preferably to 135 to 200° C., and most preferably to 150 to 185° C., is effected to carry out secondary cross-linkage. The afterheating time is limited by the point at which the desired property characteristics of the superabsorber is destroyed again because of heat damage.

The surface cross-linkage may be carried out at elevated temperature and, optionally, several times.

Owing to the special structure of the cross-linking agents to be used according to the present invention, the polymers—already without added re-cross-linkers—have an increased absorption under load merely by means of tempering, an effect typical for secondary cross-linkage.

Superabsorbers manufactured according to the present invention show a combination of favorable properties which has not been achieved as yet. The positive influence of the cross-linking agents according to the present invention stabilizes the polymer's high retention already present prior to secondary cross-linkage to such an extent that—after secondary surface cross-linkage—a retention of at least 26 g/g, preferably at least 28 g/g, and most preferably at least 30 g/g is measured.

The superabsorbers according to the present invention have a high permeability which amounts to $10 \cdot 10^{-7}$ cm$^3$ sec./g, preferably at least $15 \cdot 10^{-7}$ cm$^3$ sec./g, and most preferably at least $25 \cdot 10^{-7}$ cm$^3$ sec./g.

After liquid absorption, which preferably takes place at a rate of less than 70 sec., the swollen gel particles stand out for a dry handle, i.e., they do not have the undesired wet, tacky surface resulting from insufficient cross-linkage/secondary cross-linkage. The liquid absorption under a load (AUL) of 49 g/cm$^2$ (0.7 psi) is greater than 20 g/g, preferably greater than 23 g/g, and most preferably greater than 25 g/g.

The polymers according to the present invention have a high swelling pressure, after a measuring time of 20 minutes it amounts to at least 600 g, preferably at least 900 g, and most preferably greater than 1,000 g.

The hydrophilic superabsorbers according to the present invention are used wherever aqueous liquids are to be absorbed. They are used, for example, in hygienic articles in the form of diapers for babies and incontinence products for adults, sanitary napkins, wound patches, food packages, agriculture in the cultivation of plants, cable insulation, absorbent sheet materials made of paper, water-soluble polymers and thermoplastic materials and foams, and as active substance carriers with a retarded release to the environment.

According to their intended application, different screening fractions are used to process the superabsorbers; for example, for diapers between 100 and 800μ, for cable insulation below 100μ, i.e., if they are used in cables, the fine portions of the superabsorbers are favorable because of their tendency to "gel blocking" which blocks water penetrating into the cable. In case of diapers, this effect is undesirable since it impairs liquid absorption and distribution, for this reason coarser screening fractions are chosen.

The examples that follow will illustrate the manufacture and the properties of the polymers according to the present invention; the chapter "Test methods" describes the directions for determining the properties of the superabsorbers.

TEST METHODS

1. Retention (TBT)

Retention is determined according to the tea bag test method. 200 mg test substance is enclosed into a tea bag and immersed into 0.9%-wt. NaCl-solution for 30 minutes, followed by dripping for 10 minutes, centrifuging in a centrifuge (diameter 23 cm, 1,400 rpm) for 5 minutes, and weighing. One tea bag without water-absorbent polymer is used as so-called blank.

$TBT$=(Weight−Blank reading)/Initial weight (g/g).

Liquid Absorption under Pressure (AAP):

A water-absorbent polymer's capability of absorbing a liquid from a reservoir under a defined pressure (Absorption Against Pressure (0.3 psi=21 g/cm$^2$), AAP (0.7 psi=49 g/cm$^2$) is determined as follows: 900 mg test substance is weighed into a plastic cylinder (inner diameter=6 cm, height=5 cm) having a sieve fabric (mesh size=400 mesh) as bottom, uniformly distributed, and loaded with a defined weight in the form of a plastic plate (diameter=5.98 cm) together with a metal punch (diameter=5.98 cm). The plastic plate is located between test substance and metal punch. The whole test unit is then placed on a glass filter plate (diameter=12 cm, porosity=0) which is covered with a filter paper and impregnated with 0.9% NaCl-solution. The filter plate lies in the NaCl-solution up to its upper edge. The test substance is allowed to suck liquid for 60 minutes:

$AAP$(0.3 or 0.7 psi)=(weight of test unit prior to sucking-weight of test unit after sucking)/initial weight of test substance (g/g).

Swelling pressure (SP):

The swelling pressure is determined in a Stevens-LFRA Texture Analyser (Setting:Speed: 1.0 mm/sec.; Distance 00; Hold-position). To this end, 0.500 g of the powder (size fraction 300 to 600 mm) is weighed into the measuring cylinder having a height of 7.4 cm and a diameter of 2.7 cm, and 10 ml of 0.9% common-salt solution is added. Then, the measuring body (height 3.5 cm, diameter 2.5 cm) is driven into the cylinder such that a cavity of 6.8 ml for the gel to swell remains. The swelling pressure SP is measured after 20 minutes.

4. Rate of Liquid Absorption (SR)

In this test the time is measured wherein 1 g of superabsorber sucks 20 g of a 0.9% common-salt solution at room temperature. The mechanism of this test is described in EP 443 627, page 12, "Free-Swell-Rate".

5. Permeability (GLP)

The permeability of a swollen gel layer under a pressure load of 0.3 psi is determined as Gel-Layer-Permeability (GLP)—described in EP 0 640 330—of a swollen gel layer of superabsorbent polymer as follows.

To this end, a test unit is used which differs in the following points from the AAP(0.3 psi)-test unit described above. A glass filter plate (diameter=5.98 cm, porosity=0) and a perforated plastic plate (diameter=5.98 cm, 24 holes) having a central concentric cylinder (length=7 cm, diameter=1.8 cm) used as a spacer to the weight to be placed thereon are used instead of the plastic plate located between test substance and metal punch. For determination purposes, 900 mg of test substance is weighed into a plastic cylinder with sieve fabric as bottom (as described above), distributed uniformly, and loaded with a defined weight in the form of the glass filter plate, the perforated plate provided with spacer, and a metal punch placed on the spacer. The whole test unit is then placed on a glass filter plate (diameter=12 cm, porosity=0) which is covered with a filter paper and impregnated with a synthetic urine solution. The filter plate lies in the synthetic urine solution up to its upper edge. The test substance is allowed to suck the test substance for 60 minutes. After that, the test unit is removed from the synthetic urine solution. Then the gel layer is coated with 0.69% NaCl-solution such that there is a distance of 5 cm between the lower edge of the gel layer and the liquid level, providing a certain hydrostatic pressure. This pressure is maintained during the whole measurement by means of an appropriate device. The flow (g-NaCl-solution/sec) is automatically recorded at certain time intervals.

$GLP=(F_g(t=0)·L_0)/(d·A·WP)(cm^3·sec./g)$ wherein $F_g$ (t=0) represents the flow of the NaCl-solution in g/sec., this is obtained by means of a regression analysis of the data $F_g(t)$ of flow determinations by extrapolation against t=0; $L_0$ represents the thickness of the gel layer in cm, d the density of the NaCl-solution in g/cm$^3$, A the surface of the gel layer in cm$^2$, and WP the hydrostatic pressure over the gel layer in dyne/cm$^2$.

EXAMPLES

Examples of preparing the cross-linking agents according to the present invention:

Example 1
1,3-bis-(diallylamino)-2-propanol (TAAP)

The synthesis is described in patent document FR 2063686.

Example 2a

Reaction of polyethylene glycol(400)diglycidyl ether with diallylamine=polyethylene glycol-400-di(N,N-diallyl-3-amino-2-hydroxy-prop-1-yl)ether (PEG400DAAHPE)

2.1 g diazabicyclo[2.2.2]octane used as catalyst and 291.5 g (3.0 mol) diallylamine are added under stirring to 790 g (1.5 mol) polyethylene glycol (400) diglycidyl ether (in 200 ml ethyl acetate). The solution is refluxed for 5 h (about 100° C. internal temperature), and volatile components are withdrawn at the rotary evaporator under water-jet vacuum. A reddish brown liquid is obtained which solidifies in the refrigerator.

Yield: 1,067 g (about 99% of theory)

Example 2b

Reaction of ethylene glycol diglycidyl ether with diallylamine=ethylene glycol-di(N,N-diallyl-3-amino-2-hydroxy-prop-1-yl)ether (EGDAAHPE)

2.1 g diazabicyclo[2.2.2]octane used as catalyst and 291.5 g diallylamine are added under stirring to 260 g ethylene glycol diglycidyl ether in 200 ml ethyl acetate. The solution is refluxed for 5 h (about 90° C. internal temperature), and volatile components are withdrawn at the rotary evaporator under water-jet vacuum. A dark brown liquid obtained.

Yield: 526 g (about 95% of theory)

Example 3
1-allyloxy-2-hydroxy-3-N,N-diallylaminopropane (ADAAP)

The synthesis is described in patent document FR 2063686.

Example 4
5-EO-1,3-bis(diallylamino)-2-propanol (TAAP-5EO)

250 g 1,3-bisdiallylamino-2-propanol (1 mol) was mixed together with 3 g KOH-powder (85% dry substance); during heating the reactor content was rendered inert by applying five times 5 bar nitrogen and depressurizing to normal pressure. Subsequently, 220 g (5 mol) ethylene oxide was inserted at 110° C. up to a pressure of 4 bar. After 2 hours, the reaction was terminated, and the reactor content was taken off as yellow oil (468 g).

Hydroxyl number: 168 mg KOH/g

Example 5
10-EO-1,3-bis(diallylamino)-2-propanol (TAAP-10EO)

250 g 1,3-bisdiallylamino-2-propanol (1 mol) was mixed together with 3 g KOH-powder (85% dry substance); during heating the reactor content was rendered inert by applying five times 5 bar nitrogen and depressurizing to normal pressure. Subsequently, 440 g (10 mol) ethylene oxide was inserted at 110° C. up to a pressure of 4 bar. After 2 hours, the reaction was terminated, and the reactor content was removed as yellow oil (786 g).

Hydroxyl number: 112 mg KOH/g

Example 6
10-EO-1-allyloxy-3-(diallylamino)-2-propanol (ADAAP-10EO)

211 g 1-allyloxy-3-(diallylamino)-2-propanol (1 mol) was mixed together with 3 g KOH-powder (85% dry substance); during heating the reactor content was rendered inert by applying five times 5 bar nitrogen and depressurizing to normal pressure. Subsequently, 440 g (10 mol) ethylene oxide was inserted at 110° C. up to a pressure of 4 bar. The reaction was terminated after 2 hours, and the reactor content was taken off as yellow oil (650 g).

Hydroxyl number: 118 mg KOH/g

Example 7
10-EO-polyethylene glycol-400-di(N,N-diallyl-3-amino-2-hydroxy-prop-1-yl) ether (PEG400DAAHPE-10EO)

361 g polyethylene glycol-400-di(N,N-diallyl-3-amino-2-hydroxy-prop-1-yl)ether (PEG400DAAHPE; 0.5 mol) was mixed together with 3 g KOH-powder (85% dry substance); during heating the reactor content was rendered inert by applying five times 5 bar nitrogen and depressurizing to normal pressure. Subsequently, 220 g (5 mol) ethylene oxide was inserted at 110° C. up to a pressure of 4 bar. The reaction was terminated after 3 hours, and the reactor content was taken off as yellow oil (580 g).

Hydroxyl number: 64 mg KOH/g

Example 8
20-EO-polyethylene glycol-400-di(N,N-diallyl-3-amino-2-hydroxy-prop-1-yl) ether (PEG40DAAHPE-20EO)

361 g polyethylene glycol-400-di(N,N-diallyl-3-amino-2-hydroxy-prop-1-yl)ether (PEG400DAAHPE; 0.5 mol) was mixed together with 3 g KOH-powder (85% dry substance); during heating the reactor content was rendered inert by applying five times 5 bar nitrogen and depressurizing to normal pressure. Subsequently, 440 g (10 mol) ethylene oxide was introduced at 110° C. up to a pressure of 4 bar. After 3.5 hours the reaction was terminated, and the reactor content was removed as yellow oil (802 g).

Hydroxyl number: 46 mg KOH/g

Example 9
10-EO-ethylene glycol di(N,N-diallyl-3-amino-2-hydroxy-prop-1-yl)ether (EGDAAHPE-10EO)

369 g ethylene glycol di(N,N-diallyl-3-amino-2-hydroxy-prop-1-yl)ether (EGDAAHPE; 1.0 mol) was mixed together with 3 g KOH-powder (85% dry substance); during heating the reactor content was rendered inert by applying five times 5 bar nitrogen and depressurizing to normal pressure. Subsequently, 440 g (10 mol) ethylene oxide was inserted at 110° C. up to a pressure of 4 bar. The reaction was terminated after 3 hours, and the reactor content was removed as yellow oil (809 g).

Hydroxyl number: 94 mg KOH/g

EXAMPLES OF PREPARING SUPERABSORBERS

Example 10

An aqueous acrylic acid solution comprising 0.15% TAAP, relative to acrylic acid, was neutralized with sodium hydroxide solution (50%) under cooling. The acrylic acid concentration of the monomer solution amounted to 30% and the neutralization degree to 70 mol-%. 853.2 g of the monomer solution was cooled to 5° C. and purged with nitrogen for 10 minutes. After that, 177 mg tert-butyl hydroperoxide (70%) (dissolved in 10 g water), 500 mg sodium peroxodisulfate (dissolved in 8 g water), 177 mg 2,2'-azobis-(isobutyronitrile) (dissolved in 10 g water), and 8 mg ascorbic acid (dissolved in 2 g water) were added one after the other. Polymerization started immediately, and the temperature of the resulting gel mass was raised to about 100° C. After 30 minutes, the gel block was comminuted and dried at 150° C. for 2 hours in a hot-air drying cabinet. The polymer was then ground and screened out to a size fraction of 150 to 850 μm.

The powdery polymer was coated with a solution consisting of 0.5% ethylene carbonate/2% water/4% ethanol, relative to polymer, by intense mixing, and then heated at 180° C. in an oven for 20, 30 and 40 minutes, respectively.

Examples 11–29

Performance of these Examples as in Example 10; however, other concentrations and types of cross-linking agents were used. The compositions and properties are listed in Tables 2 and 3. The abbreviation TMPTA stands for trimethylolpropane triacrylate.

Examples 30–32

The secondary cross-linking effect of the precross-linkers according to the present invention in subsequent tempering is to be shown. To this end, the starting products from Example 14, 22, and 26 which have not been re-cross-linked were subjected to a heat treatment at 180° C. for 30 minutes and then examined as to retention and AAP 21. A distinct change in properties was found which is typical for a secondary cross-linkage. The results are shown in Table 4.

Comparative Example 1

Commercial products were examined with respect to their retention and permeability properties. Without exception, there were poor permeabilities, irrespective of the retention.

TABLE 1

| Manufacturer/Product | Retention (g/g) | GLP ($10^{-7}$ cm$^3$ sec/g) |
|---|---|---|
| Atochem/AK 94 EX006 | 30.5 | 0 |
| Allied Colloids/CKH 5164A | 39.5 | 1 |
| Allied Colloids/Salsorb CL20 | 30.5 | 6 |
| Chemdal/ASAP 2000 | 31.0 | 6 |
| Hoechst/IM 7000 | 35.0 | 0 |
| Mitsubishi/US 50 | 34.5 | 3 |
| BASF/Aqualic LF76 | 31.0 | 1 |

Examples 33–38

Polymerization is carried out according to the following guideline; re-cross-linking is effected as in Examples 10–29:

In a cylindrical plastic vessel a polymerization batch totaling 1,000 g is prepared. 280 g acrylic acid as well as the cross-linking agents, comonomers, and further components to be used are prepared in demineralized water. Under stirring and cooling, partial neutralization to a neutralization degree of 70% is carried out with 50% sodium hydroxide solution. The solution is cooled to 7–8° C., and nitrogen is bubbled through until the oxygen content in the monomer solution has dropped to a value of below 0.2 ppm. Subsequently, 100 ppm azo-bis(2-amidinopropane) dihydrochloride, dissolved in 10 g demin. water, 300 ppm sodium persulfate, dissolved in 6 g demin. water, 70 ppm hydrogen peroxide (35%), dissolved in 1 g demin. water, are added. Polymerization is then started by adding 9 ppm ascorbic acid, dissolved in 2 g demin. water, whereupon the temperature clearly rises. After termination of the polymerization, the gel-like polymer block is comminuted, minced, and dried. After that, the polymer is ground and screened out to the grain fraction of 150–800μ.

The composition of the superabsorbers with respect to cross-linking agents and product properties are listed in Table 5.

TABLE 2

| | | | | TBT (Ret) (g/g) | | | | | |
|---|---|---|---|---|---|---|---|---|---|
| Ex. | Cross-linking agent | | start. | re-cr.-linked | re-cr.-linked | re-cr.-linked | AAP (g/g) | | GLP |
| No. | type | %-wt. | prod. | (180°/20') | (180°/30') | (180°/40') | 21 g/cm$^2$ | 49 g/cm$^2$ | ($10^{-7}$ cm$^3$ sec/g) |
| 10 | TAAP | 0.15 | 38.1 | 32.4 | 30.1 | 31.4 | 28.2 | 22.9 | 30 |
| 11 | TAAP/TMPTA | 0.15/0.05 | 36.7 | 32.6 | 31.7 | 30.8 | 30.2 | 23.2 | 16 |
| 12 | TAAP-5EO | 0.28 | 41.6 | 32.1 | 30.6 | 30 | 31 | 25 | 26 |
| 13 | TAAP-5EO/TMPTA | 0.28/0.05 | 40.1 | 31.6 | 30.3 | 29.6 | 32.5 | 26.6 | 14 |
| 14 | TAAP-10EO | 0.41 | 39.2 | 31 | 29.3 | 29.3 | 30.1 | 25.5 | 29 |
| 15 | TAAP-10EO/TMPTA | 0.41/0.05 | 39.2 | 31.3 | 29.8 | 28.4 | 31.3 | 25.6 | 27 |
| 16 | ADAAP | 0.225 | 33.9 | 30 | 29 | 29 | 30.9 | 23.9 | 27 |
| 17 | ADAAP/TMPTA | 0.225/0.05 | 34 | 30.3 | 29.6 | 28.6 | 31.1 | 24.9 | 11 |
| 18 | ADAAP-10EO | 0.225 | 48.5 | 37.4 | 33.8 | 33.1 | 29.7 | 21.0 | 12 |
| 19 | ADAAP-10EO/TMPTA | 0.225/0.05 | 43.0 | 33.9 | 30.9 | 30.6 | 29.8 | 23.3 | 6 |
| 20 | EGDAAHPE | 0.2 | 36.6 | 29.4 | 28.6 | 28.3 | 29.1 | 23.4 | 20 |
| 21 | EGDAAHPE/TMPTA | 0.2/0.05 | 36.5 | 31.7 | 30.3 | 30.3 | 31.7 | 24.9 | 10 |
| 22 | EGDAAHPE-10EO | 0.44 | 39.6 | 28.5 | 26.2 | 25.4 | 22.9 | 19.1 | 30 |
| 23 | EGDAAHPE-10EO/TMPTA | 0.44/0.05 | 36.2 | 27.9 | 28.3 | 26.2 | 29.0 | 24.0 | 29 |
| 24 | PEG400DAAHPE | 0.4 | 36.6 | 30.7 | 30.2 | 28.8 | 30.3 | 23.6 | 16 |
| 25 | PEG400DAAHPE/TMPTA | 0.4/0.05 | 33.9 | 29 | 28.5 | 26.8 | 29.6 | 24.6 | 23 |
| 26 | PEG400DAAHPE-10EO | 0.61 | 38.0 | 28.8 | 26.9 | 25.6 | 24.3 | 21.0 | 14 |
| 27 | PEG400DAAHPE-10EO/TMPTA | 0.61/0.05 | 36.4 | 29.2 | 27.9 | 26.3 | 24.6 | 21.0 | 26 |
| 28 | PEG400DAAHPE-20EO | 0.61 | 49.5 | 33.7 | 32.1 | 29.2 | 29.7 | 21.8 | 9 |
| 29 | PEG400DAAHPE-20EO/TMPTA | 0.61/0.05 | 42.1 | 31.5 | 29.7 | 30.8 | 28.2 | 22.6 | 20 |

TABLE 3

| Example | TBT (g/g) | AAP (21 g/cm$^2$) (g/g) | AAP (49 g/cm$^2$) (g/g) | SR (sec.) | SP (20') (g) | SP (120') (g) |
|---|---|---|---|---|---|---|
| 10 | 30.1 | 28.2 | 22.9 | | 1110 | 695 |
| 11 | 31.7 | 30.2 | 23.2 | | 960 | 670 |
| 12 | 30.6 | 31.0 | 25.0 | | 1240 | 810 |

TABLE 3-continued

| Example | TBT (g/g) | AAP (21 g/cm²) (g/g) | AAP (49 g/cm²) (g/g) | SR (sec.) | SP (20') (g) | SP (120') (g) |
|---|---|---|---|---|---|---|
| 13 | 30.3 | 32.5 | 26.6 | 65 | 1250 | 875 |
| 14 | 29.3 | 30.1 | 25.5 |  | 1250 | 925 |
| 15 | 29.8 | 31.3 | 25.6 |  | 1440 | 905 |
| 16 | 29.0 | 30.9 | 23.9 | 74 | 1000 | 650 |
| 17 | 29.6 | 31.1 | 24.9 |  | 830 | 580 |
| 18 | 33.8 | 29.7 | 21.0 |  | 1050 | 710 |
| 19 | 30.9 | 29.8 | 23.3 |  | 1440 | 730 |
| 20 | 28.6 | 29.1 | 23.4 | 62 | 975 | 695 |
| 21 | 30.3 | 31.7 | 24.9 | 60 | 930 | 665 |
| 22 | 26.2 | 22.9 | 19.1 |  | 1025 | 710 |
| 23 | 28.3 | 29.0 | 24.0 |  | 950 | 660 |
| 24 | 30.2 | 30.3 | 23.6 | 65 | 840 | 600 |
| 25 | 28.5 | 29.6 | 24.6 | 63 | 1025 | 780 |
| 26 | 26.9 | 24.3 | 21.0 | 55 | 1020 | 715 |
| 27 | 27.9 | 24.6 | 21.0 |  | 960 | 600 |
| 28 | 32.1 | 29.7 | 21.8 | 61 | 1125 | 680 |
| 29 | 29.7 | 28.2 | 22.6 |  | 1150 | 725 |

TABLE 4

| Example | start. prod. Ex. | start. prod.-TBT (g/g) | start. prod.-AAP 21 (g/g) | afterheated-TBT (g/g) | afterheated-AAP21 (g/g) |
|---|---|---|---|---|---|
| 30 | 14 | 39.2 | 9.0 | 33.9 | 18.1 |
| 31 | 22 | 39.6 | 7.8 | 29.4 | 20.8 |
| 32 | 26 | 38.0 | 8.4 | 27.2 | 21.9 |

TABLE 5

| Example | cross-linker type (% monomer) | start. prod.-TBT | re-cr.-linked-TBT | re-cross-linked-AAP (21 g/cm²) | re-cross-linked-AAP (49 g/cm²) |
|---|---|---|---|---|---|
| 33 | 0.15/ADAAP-10EO | 39.7 | 29.9 | 30.4 | 23.6 |
| 34 | 0.61/PEG400DAAHPE-10EO | 31.8 | 24.2 | 25.7 | 21.7 |
| 35 | 0.61/PEG400DAAHPE-20EO | 40.2 | 28.1 | 29.5 | 24.1 |
| 36 | 0.61/EGDAAHPE-10EO | 31.6 | 24.5 | 26.2 | 21.9 |
| 37 | 0.15/TAAP | 32.7 | 28.0 | 29.5 | 22.7 |
| 38 | 0.15/TAAP-10EO | 32.1 | 26.9 | 28.5 | 23.3 |

We claim:

1. A cross-linked polymer obtained by polymerizing partially neutralized, monoethylenically unsaturated, acid groups-containing monomers, optionally with further monomers copolymerizable therewith, and optionally with graft polymerizable polymers, in the presence of cross-linking agents of at least one polyunsaturated amino alcohol.

2. The polymer according to claim 1 wherein the cross-linking agents are reaction products of (meth)allylamines with monoglycidyl compounds and optional alkylene oxide, which may be described by the general formula I $H_oR_3(NR_1R_2)_p$ $R_1,R_2$: CHR=CH—CH$_2$, H   for o = 0 is p = 2
$R$: H, CH$_3$   for o = 1 is p = 1
$R_3$: $R_a$-C(H)$_c$(R$_6$)—CH$_2$
$R_a$: monovalent for c = 0: H
divalent for c = 1: CH$_2$,
OCH$_2$,
C$_{1-6}$—O—(CHR—CHR—O)$_d$, -continued

d = 1–45
C$_{1-6}$—CO—O—(CHR—CHR—O)$_d$
$R_6$: $R_7$H
$R_7$: O, O(CHR—CHR—O)$_n$   n: 1 to 45, with the proviso that at least 2 residues $R_1,R_2$ mean CHR=CH—CH$_2$.

3. The polymer according to claim 1, wherein the cross-linking agents are reaction products of (meth)allylamines with di-, tri-, or tetraglycidyl compounds and optional alkylene oxide, which can be described by the general formula II

| $R_8(NR_1R_2)_2$ |
|---|
| $R_1, R_2$: CHR=CH—CH$_2$, H |
| R: H, CH$_3$ |
| $R_8$: CH$_2$—CH(R$_6$)—CH$_2$—O—R$_4$—CH$_2$—CH(R$_6$)—CH$_2$ |
|     $R_4$: (CHR—CHR—O)$_m$,      m = 1 to 45 |
|            C$_1$–C$_6$—O, |
|            R$_5$(O—R$_3$—NR$_1$R$_2$)$_r$—O |
|                             r = 0: if diglycide compounds are used |
|                             r = 1: if triglycide compounds are used |
|                             r = 2: if tetraglycide compounds are used |
|     $R_5$: alkylene residue of a polyol, optionally with one or two OH-functions which may optionally be reacted with up to 45 moles of alkylene oxide |
| $R_3$: CH$_2$—CH(R$_6$)—CH$_2$ |
|     $R_6$: R$_7$H |
|          $R_7$: O, O(CHR—CHR—O)$_n$      n: 1 to 45, | with the proviso that at least 2 residues $R_1, R_2$ mean CHR=CH—CH$_2$.

4. The polymer according to claim 1 wherein the cross-linking agents are reaction products of (meth)allylamines or saturated primary amines with (meth)acrylglycide esters and/or (meth)allyl glycidyl ethers and optional alkylene oxide, which can be described by the general formula III

| $(R_9—R_3)_a N(B)_c (R_1)_j (R_2)_k$ | |
|---|---|
| B: C$_1$–C$_6$-alkyl | for c = 0 the following is valid: |
| $R_9$: CHR=CH—CH$_2$—O, | for a = 1 is j = 1 and k = 1 |
|       CH$_2$=CR—CO—O | for a = 2 is j = 1 and k = 0 |
| $R_1, R_2$: CHR=CH—CH$_2$, H | for a = 3 is j and k = 0 |
| R: H, CH$_3$ | |
| | for c = 1 the following is valid: |
| $R_3$: CH$_2$—CH(R$_6$)—CH$_2$ | for a = 1 is j = 1 and k = 0 |
|     $R_6$: R$_7$H | a = 2 is j and k = 0 |
|          $R_7$: O, O(CHR—CHR—O)$_n$ | |
|              n: 1 to 45 | |

5. The polymer according to claim 1 characterized in that the cross-linking agents are reaction products of di- or polyamines with (meth)allyl glycidyl ethers and/or (meth)acrylglycide esters and optional alkylene oxides, which can be described by the general formula IV

| $R_{11}[N(A)_b—(R_3—R_9)_p]_z$ |
|---|
| for b = 1 is p = 1 |
| for b = 0 is p = 2 |
| z = 2, 3, 4 |
| A: H, C$_1$–C$_6$-alkyl |
| $R_3$: CH$_2$—CH(R$_6$)—CH$_2$ |
|     $R_6$: R$_7$H |
|          $R_7$: O, O(CHR—CHR—O)$_n$    n: 1 to 45 |
|          R: H, CH$_3$ |
| $R_9$: CHR=CH—CH$_2$—O, |
|       CH$_2$=CR—CO—O |
| $R_{11}$: di-, tri- or tetravalent alkylene residue of the amine component (mixed or individually aliphatic, cycloaliphatic, aromatic, heterocyclic). |

6. The polymer according to claim 1 wherein the cross-linking agents comprise at least one (meth) allyl group.

7. The polymer according to claim 1 wherein the polyunsaturated amino alcohol comprises 1,3-bis-(diallylamino)-2-propanol.

8. The polymer according to claim 1 wherein the polyunsaturated amino alcohol comprises polyethylene glycol di(N,N-diallyl-3-amino-2-hydroxy-prop-1-yl)ether.

9. The polymer according to claim 1 wherein the polyunsaturated amino alcohol comprises 1-allyloxy-2-hydroxy-3-N,N-diallyl-aminopropane.

10. The polymer according to claim 1 wherein the cross-linking agents are additionally alkoxylated.

11. The polymer according to claim 10 wherein the cross-linking agents are reacted with up to 45 moles of alkylene oxide, per mole of hydroxyl group.

12. The polymer according to claim 1, wherein the cross-linking agents or their mixtures are used in amounts of 0.01–3.0%-wt., relative to the monomers.

13. The polymer according to claim 1, wherein further cross-linkers are used in amounts of 0–1%-wt., relative to the monomers.

14. The polymer according to claim 13 wherein at least one of triallylamine, N,N-methylenebisacrylamide, bis(acrylamido) acetic acid, allyl (meth)acrylate, trimethylolpropane triacrylate, ethoxylated trimethylolpropane triacrylate, polyglycol diacrylate are used as co-cross-linkers.

15. The polymer according to claim 1 wherein the unsaturated, acid groups-containing monomers are selected from the group consisting of acrylic acid, methacrylic acid, vinyl acetic acid, vinyl sulfonic acid, methallyl sulfonic acid, and 2-acrylamido-2-methylpropane sulfonic acid.

16. The polymer according to claim 1 which additionally comprises incorporated by polymerization 0 to 40%-wt., relative to the acid monomers, of further comonomers selected from the group consisting of (meth)acrylamide, (meth)acrylonitrile, vinyl pyrrolidone, hydroxyethyl acrylate, and vinyl acetamide.

17. The polymer according to claim 1 which additionally comprises up to 30%-wt., relative to the sum of existing, monomers, of a water-soluble graft-polymerizable polymer.

18. The polymer according to claim 1 which has been cross-linked at the surface at least one time with a secondary cross-linking agent.

19. The polymer according to claim 18 which has been cross-linked at the surface with a secondary cross-linking agent selected from the group consisting of polyols, polyepoxides, polyamines, and alkylene carbonates.

20. The polymer according to claim 18 which has a retention of at least 30 g/g, a liquid absorption under pressure (49 g/cm$^2$) of at least 20 g/g, a permeability GLP of at least $10 \cdot 10^{-7}$ cm$^3$ sec./g, and a swelling pressure (20 min.) of at least 600 g.

21. The polymer according to claim 18 which has a permeability GLP of at least $15 \cdot 10^{-7}$ cm$^3$ sec./g.

22. The polymer according to claim 18 which has a swelling pressure (20 min.) of at least 900 g.

23. The polymer according to claim 18 which has a liquid absorption under pressure (49 g/cm$^2$) of at least 23 g/g.

24. A process for the production of a cross-linked polymer according to claim 1, comprising polymerizing by solution or suspension polymerization unsaturated, acid groups-containing, partially neutralized monomers in an aqueous solution to form a hydrogel, wherein said polymerizing is in the presence of cross-linking agents of at least one polyunsaturated amino alcohol and optional further cross-linkers under addition of radical formers, and wherein after said polymerizing, the polymer is comminuted, dried, ground, and screened out.

25. The process according to claim 24 polymer is treated with at least one surface cross-linking agent, and that a surface cross-linkage is carried out at elevated temperatures.

26. The process according to claim 25 wherein the surface treatment and the cross-linkage are carried out several times.

27. A cross-linking agent according to the general formula I

| $H_oR_3(NR_1R_2)_p$ | | |
|---|---|---|
| $R_1,R_2$: | CHR=CH—CH$_2$, H | for o = 0 is p = 2 |
| R: | H, CH$_3$ | for o = 1 is p = 1 |
| $R_3$: | $R_a$—C(H)$_c$(R$_6$)—CH$_2$ | |
| $R_a$: | monovalent for c = 0: | H |
| | divalent for c = 1: | CH$_2$, |
| | | OCH$_2$, |
| | | C$_{1-6}$—O—(CHR—CHR—O)$_d$, d = 1–45 |
| | | C$_{1-6}$—CO—O—(CHR—CHR—O)$_d$ |
| $R_6$: | $R_7$H | |
| $R_7$: | O, O(CHR—CHR—O)$_n$ | n: 1 to 45, | with the proviso that at least 2 residues $R_1, R_2$ mean CHR=CH—CH$_2$.

28. A cross-linking agent according to the general formula II

| $R_8(NR_1R_2)_2$ | | |
|---|---|---|
| $R_1,R_2$: | CHR=CH—CH$_2$, H | |
| R: | H, CH$_3$ | |
| $R_8$: | CH$_2$—CH(R$_6$)—CH$_2$—O—R$_4$—CH$_2$—CH(R$_6$)—CH$_2$ | |
| $R_4$: | (CHR—CHR—O)$_m$, | m = 1 to 45 |
| | C$_1$–C$_6$—O, | |
| | R$_5$(O—R$_3$—NR$_1$R$_2$)$_r$—O | |
| | | r = 0: if diglycide compounds are used |
| | | r = 1: if triglycide compounds are used |
| | | r = 2: if tetraglycide compounds are used |
| $R_5$: | alkylene residue of a polyol, optionally with one or two OH-functions which may optionally be reacted with up to 45 moles of alkylene oxide | |
| $R_3$: | CH$_2$—CH(R$_6$)—CH$_2$ | |
| $R_6$: | $R_7$H | |
| $R_7$: | O, O(CHR—CHR—O)$_n$ | n: 1 to 45, | with the proviso that at least 2 residues $R_1, R_2$ mean CHR=CH—CH$_2$.

29. A cross-linking agent according to the general formula III

| $(R_9$—$R_3)_aN(B)_c(R_1)_j(R_2)_k$ | | |
|---|---|---|
| B: | C$_1$–C$_6$-alkyl | for c = 0 the following is valid: |
| $R_9$: | CHR=CH—CH$_2$—O, | for a = 1 is j = 1 and k = 1 |
| | CH$_2$=CR—CO—O | for a = 2 is j = 1 and k = 0 |
| $R_1,R_2$: | CHR=CH—CH$_2$, H | for a = 3 is j and k = 0 |
| R: | H, CH$_3$ | |
| | | for c = 1 the following is valid: |
| $R_3$: | CH$_2$—CH(R$_6$)—CH$_2$ | for a = 1 is j = 1 and k = 0 |
| $R_6$: | $R_7$H | a = 2 is j and k = 0 |
| $R_7$: | O, O(CHR—CHR—O)$_n$ | |
| | n: 1 to 45 | |

30. A cross-linking agent according to the general formula IV

| $R_{11}[N(A)_b$—$(R_3$—$R_9)_p]_z$ | |
|---|---|
| | for b = 1 is p = 1 |
| | for b = 0 is p = 2 |
| | z = 2, 3, 4 |
| A: | H, C$_1$–C$_6$-alkyl |
| $R_3$: | CH$_2$—CH(R$_6$)—CH$_2$ |
| $R_6$: | $R_7$H |
| $R_7$: | O, O(CHR—CHR—O)$_n$    n: 1 to 45 |
| R: | H, CH$_3$ |
| $R_9$: | CHR=CH—CH$_2$—O, |
| | CH$_2$=CR—CO—O |
| R11: | di-, tri- or tetravalent alkylene residue of the amine component (mixed or individually aliphatic, cycloaliphatic, aromatic, heterocyclic). |

31. The cross-linking agent according to claim 28 wherein the amine functions are quaternized.

32. The polymer according to claim 10, wherein the amine functions are quaternized.

33. The polymer according to claim 11, wherein the amine functions are quaternized.

34. The cross-linking agent according to claim 27, wherein the amine functions are quaternized.

35. The cross-linking agent according to claim 29, wherein the amine functions are quaternized.

36. The cross-linking agent according to claim 30, wherein the amine functions are quaternized.

37. The polymer according to claim 11, wherein the cross-linking agents are reacted with up to 20 moles of alkylene oxide.

38. The polymer according to claim 11, wherein the cross-linking agents are reacted with up to 12 moles of alkylene oxide.

39. The polymer according to claim 12, wherein said amounts are 0.05–1.5%-wt.

40. The polymer according to claim 12 wherein said amounts are 0.1–1.0%-wt.

41. The polymer according to claim 13, wherein the amounts are 0.01–0.8%-wt.

42. The polymer according to claim 13, wherein the amounts are 0.05–0.4%-wt.

43. The polymer according to claim 17, wherein said polymer is a polysaccharide and/or polyvinyl alcohol.

44. The polymer according to claim 21, wherein the permeability GLP is at least $25 \cdot 10^{-7}$ cm$^3$ sec./g.

45. The polymer according to claim 22, wherein the swellings pressure (20 min.) is at least 1000 g.

46. A process for absorbing water or an aqueous liquid comprising absorbing said water or aqueous liquid in an absorbent obtained from the cross-linked polymer of claim 1.

* * * * *